US00PP17003P2

(12) United States Plant Patent
Arita

(10) Patent No.: US PP17,003 P2
(45) Date of Patent: Aug. 15, 2006

(54) ***COLEUS* PLANT NAMED 'KAKEGAWA CE10'**

(50) Latin Name: *Solenostemon scutellarioides*
Varietal Denomination: Kakegawa CE10

(75) Inventor: Yo Arita, San Jose (CR)

(73) Assignee: Sakata Seed Corporation, Yokohama (JP)

( * ) Notice: Subject to any disclaimer, the term of this patent is extended or adjusted under 35 U.S.C. 154(b) by 48 days.

(21) Appl. No.: 11/067,978

(22) Filed: Feb. 28, 2005

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
(74) *Attorney, Agent, or Firm*—Jondle & Associates P.C.

(57) ABSTRACT

'Kakegawa CE10' is a new *Coleus* cultivar particularly distinguished by having a unique leaf color pattern and a creeping growth habit.

1 Drawing Sheet

Genus and species: *Solenostemon scutellarioides*.
Variety denomination: 'Kakegawa CE10'.

BACKGROUND OF THE INVENTION

The present invention comprises a new and distinct cultivar of *Coleus*, botanically known as *Solenostemon scutellarioides* and hereinafter referred to by the cultivar name 'Kakegawa CE10'. It is characterized by having a unique leaf pattern and creeping growth habit. The new cultivar originated as a selection from a population resulting from self-pollination of a proprietary *Coleus* breeding line, 9CL. 9CL was self pollinated to produce S2 seed. $S_2$ seed was sown in a greenhouse in Cartago, Costa Rica. Two single-plant selections were made from the $S_2$ generation and self-pollinated to create two separate $S_3$ seed lots.

In 2000, seed from each $S_3$ lot was sown in the greenhouse. Two single-plant selections were made and self-pollinated to produce two separate $S_4$ seed lots. In 2001, seed from each $S_4$ lot was sown. One single-plant selection was made based on its creeping habit and self-pollinated to produce $S_5$ seed. In 2002, $S_5$ seed was sown and one single-plant selection was made based on its semi-creeping habit. This selection was asexually propagated through rooted plant cuttings in both Cartago, Costa Rica and Salinas, Calif. 'Kakegawa CE10' has been shown to reproduce true to type in successive generations of asexual propagation.

DESCRIPTION OF PHOTOGRAPHS

This new *Coleus* plant is illustrated by the accompanying photographs which show the plant's form and foliage. The colors shown are as true as can be reasonably obtained by conventional photographic procedures.

Figure 1:
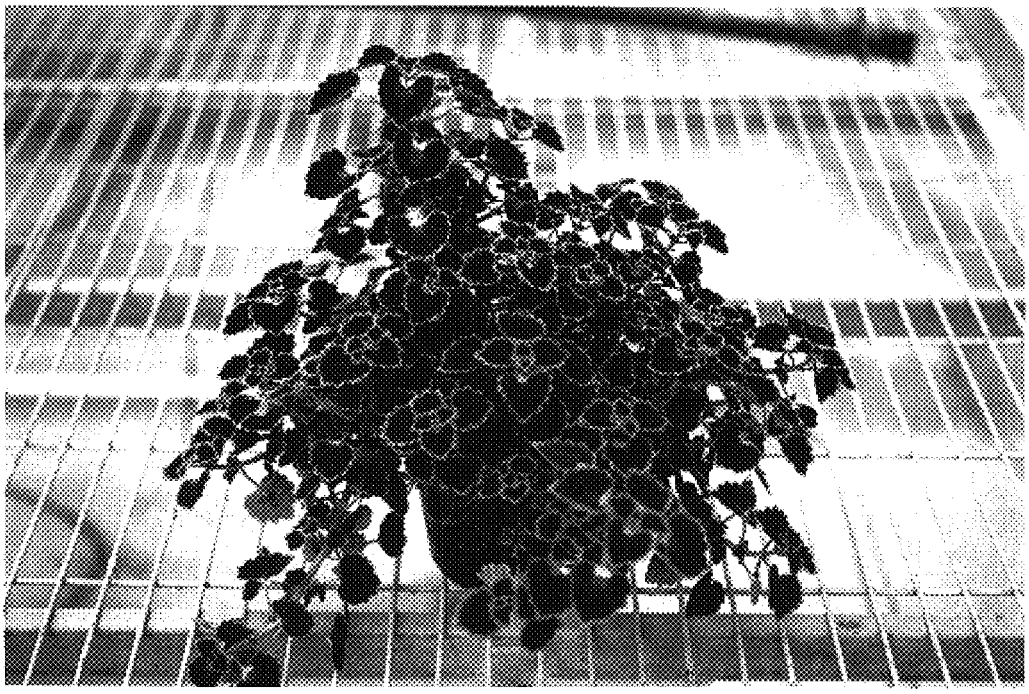

FIG. 1. shows overall plant habit.

Figure 2:
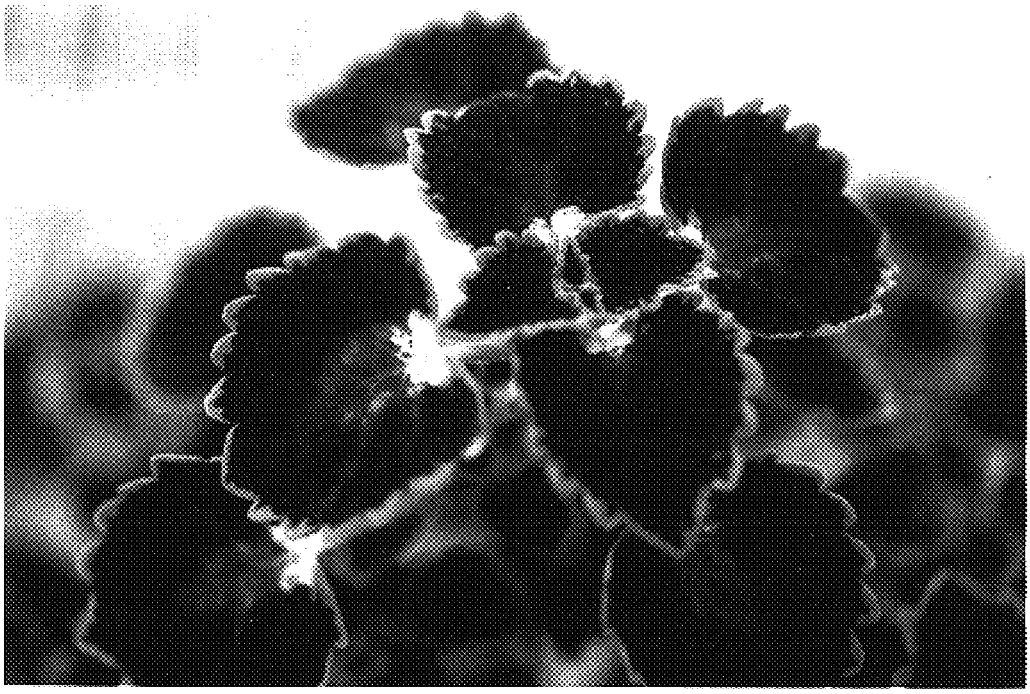

FIG. 2. shows a close-up view of the leaves.

DESCRIPTION OF THE NEW CULTIVAR

The following detailed description sets forth the distinctive characteristics of 'Kakegawa CE10'. The data which define these characteristics were collected from asexual reproductions carried out in Salinas, Calif. The detailed description was taken from plants grown under greenhouse conditions for approximately 4 months from transplanting of rooted cuttings. Color references are to the R.H.S. Colour Chart of The Royal Horticultural Society of London (R.H.S.), $4^{th}$ Edition.

DETAILED BOTANICAL DESCRIPTION

Classification:
- *Family.*—Lamiaceae Lindl.
- *Species.*—*Solenostemon scutellarioides* cultivar 'Kakegawa CE10'.
- *Common name.*—*Coleus.*

Parentage:
- *Male.*—Proprietary *Coleus* breeding line.
- *Female.*—Proprietary *Coleus* breeding line.

Plant description:
- *Form.*—Semi-creeping.
- *Habit.*—Freely branching with about 7 lateral branches.
- *Height.*—22 cm as measured from soil level to top of plant.
- *Spread.*—35 cm.

Propagation:
- *Type cuttings.*—Vegetative cuttings.
- *Time to produce a rooted cutting.*—5–6 weeks.

Environmental conditions for plant growth: The terminal 1.0–1.5 inches of actively growing stems were excised and the base of each cutting dipped for one to two seconds in a 1:9 solution of DIP 'N GROW root inducing solution immediately prior to placing the cutting into a cell tray. The cell tray contained a moistened peat moss-based growing medium. The cuttings were misted with water from overhead for 10 seconds every 30 minutes until sufficient roots were formed. Rooted cuttings were transplanted and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C. 'Kakegawa CE10' will tolerate a wide range of temperatures, from 2° C. to 35° C.

Lateral branches:

*Branch color.*—RHS 143C (green).
*Texture.*—Pubescent.
*Pubescence color.*—N155A (white).
*Stem description.*—Ancipital (round) in cross-section.
*Branch diameter.*—0.5 cm.
*Branch length.*—16.5 cm.
*Internode length.*—2.0–4.0 cm.
*Aspect.*—Spreading.

Leaves:

*Leaf arrangement.*—Opposite.
*Leaf shape.*—Deltoid/Ovate.
*Leaf apex.*—Mucronate.
*Leaf base.*—Truncate.
*Leaf margin.*—Crenate (scalloped).
*Leaf texture, both surfaces.*—Pubescent.
*Pubescence color.*—N155A (white).
*Venation.*—Pinnate.
*Leaf length.*—3.0–4.0 cm.
*Leaf width.*—3.6–4.3 cm.
*Leaf color* (*multicoloured; colors arranged in bands starting at leaf base and moving outwardly toward leaf edge*).—Developing foliage: Upper surface: base is RHS 3B (yellow); inner band is RHS 58B (red-purple); outer band is RHS 77A (purple); edge is RHS 143B (green). Lower surface: base is RHS 3C (yellow); middle band is RHS 59A (red-purple); edge is RHS 139D (green). Fully expanded foliage: Upper surface: base is RHS 77A (purple); edge is RHS 143B (green). Lower surface: base is RHS 59A (red-purple); edge is RHS 139C (green).
*Petiole length.*—2.6–3.4 cm.
*Petiole diameter.*—0.2–0.3 cm.
*Petiole color.*—RHS 143B (green).

Disease and Insect Resistance

'Kakegawa CE10' has no unique resistance or susceptibility to common Coleus pathogens or pests.

Comparison with Known Cultivars

Coleus 'Kakegawa CE10' is a distinct variety of *Coleus* due to its unique leaf color pattern and creeping growth habit. 'Kakegawa CE10' is distinguished from Breeding Line CL9 mainly by its leaf color as shown in Table 1 below.

TABLE 1

| Characteristic | 'Kakegawa CE10' | Breeding Line 9CL |
|---|---|---|
| Leaf color, upper surface | Bi-color; purple center with green edge; colors brighter than breeding line 9CL; contrast between center and edge greater than breeding line 9CL | Bi-color; burgundy center with green edge |

'Kakegawa CE10' is most similar to the *Coleus* variety 'Trailing Salamander' (Unpatented); however, there are differences in leaf color and growth habit as described in Table 2 below.

'Kakegawa CE10' is distinguished from its parental cultivars and 'Kakegawa CE9', co-pending U.S. Plant patent application Ser. No. 11/067,970 primarily in foliage coloration.

TABLE 2

| Characteristic | 'Kakegawa CE10' | 'Trailing Salamander' |
|---|---|---|
| Leaf color pattern | Multicolor; Upper (from inside to edge): yellow, pink, blotchy purple, green | Bi-color; Upper central: black, solid. Upper edge: green |
| Growth habit | Semi-creeping | Mounding |

I claim:

1. A new and distinct cultivar of *Coleus* plant as shown and described herein.

* * * * *